United States Patent
Lee et al.

(10) Patent No.: US 8,007,171 B2
(45) Date of Patent: Aug. 30, 2011

(54) METHOD AND SUPPORT DEVICE FOR MEASURING JAWBONE MINERAL DENSITY

(75) Inventors: Soo Yeul Lee, Daejeon (KR); Jeong Won Lee, Daejeon (KR); Seung Hwan Kim, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 97 days.

(21) Appl. No.: 12/506,371

(22) Filed: Jul. 21, 2009

(65) Prior Publication Data

US 2010/0142674 A1   Jun. 10, 2010

(30) Foreign Application Priority Data

Dec. 4, 2008 (KR) .................... 10-2008-0122276

(51) Int. Cl.
*A61B 6/14* (2006.01)
*G03B 42/04* (2006.01)
(52) U.S. Cl. .................. 378/169; 378/191; D24/161
(58) Field of Classification Search .............. 378/168, 378/169, 191; D24/161
See application file for complete search history.

(56) References Cited

U.S. PATENT DOCUMENTS

| | | | | |
|---|---|---|---|---|
| 3,304,423 A | * | 2/1967 | Medwedeff | 378/170 |
| 3,312,218 A | * | 4/1967 | Jacobs | 128/862 |
| 4,694,478 A | * | 9/1987 | Delnon | 378/39 |
| 4,941,164 A | * | 7/1990 | Schuller et al. | 378/205 |
| 5,090,047 A | * | 2/1992 | Angotti et al. | 378/170 |
| 5,629,972 A | * | 5/1997 | Hausmann et al. | 378/170 |
| 5,737,388 A | * | 4/1998 | Kossila | 378/168 |
| 6,690,761 B2 | * | 2/2004 | Lang et al. | 378/56 |
| D504,721 S | * | 5/2005 | Dorfman | D24/135 |
| 6,904,123 B2 | * | 6/2005 | Lang | 378/54 |
| 7,050,534 B2 | * | 5/2006 | Lang | 378/54 |
| 7,120,225 B2 | | 10/2006 | Lang et al. | |
| 7,172,339 B2 | * | 2/2007 | Diederich | 378/168 |
| 7,517,148 B2 | * | 4/2009 | Ceisel et al. | 378/191 |
| 7,599,468 B2 | * | 10/2009 | Zuendorf et al. | 378/38 |
| 7,664,298 B2 | * | 2/2010 | Lang et al. | 382/128 |
| 2002/0067798 A1 | | 6/2002 | Lang | |
| 2002/0181755 A1 | | 12/2002 | Lee et al. | |
| 2007/0025607 A1 | | 2/2007 | Takaishi | |
| 2008/0253506 A1 | | 10/2008 | Zuendorf et al. | |

FOREIGN PATENT DOCUMENTS

KR   20020086198 A   11/2002

* cited by examiner

*Primary Examiner* — Edward Glick
*Assistant Examiner* — Thomas R Artman
(74) *Attorney, Agent, or Firm* — Ladas & Parry LLP

(57) ABSTRACT

There are provided a method and support device for measuring jawbone mineral density using a jawbone X-ray image. The method for measuring jawbone mineral density includes: obtaining a jawbone X-ray image using a support device for jawbone; defining a region of interest from the obtained jawbone X-ray image; and measuring jawbone mineral density from the defined region of interest. Therefore, the support device for measuring jawbone mineral density may be useful to measure jawbone mineral density with a jawbone X-ray imaging device, which has been widely used in dental clinics, by using the method.

16 Claims, 4 Drawing Sheets

METHOD AND SUPPORT DEVICE FOR MEASURING JAWBONE MINERAL DENSITY

CROSS-REFERENCE TO RELATED APPLICATIONS

This application claims the priority of Korean Patent Application No. 2008-122276 filed on Dec. 4, 2008, in the Korean Intellectual Property Office, the disclosure of which is incorporated herein by reference.

BACKGROUND OF THE INVENTION

1. Field of the Invention

The present invention relates to a method and support device for measuring jawbone mineral density using a jawbone X-ray image. More particularly, it relates to a method and support device for measuring jawbone mineral density capable of obtaining a jawbone X-ray image using a support device and a jawbone X-ray imaging device, which has been widely used in dental clinics, and measuring jawbone mineral density from the obtained jawbone X-ray image.

2. Description of the Related Art

In the field of dental service, the necessity of measuring jawbone mineral density in connection with the diagnosis of osteoporosis has been raised for a long time. Also, the necessity of the measurement of jawbone mineral density has been steadily issued in order to evaluate the feasibility of the transplantation of artificial teeth in advance.

Osteoporosis is a morbid condition in which the quantity of bone is decreased abnormally, and is accompanied by pains, fractures of the spine and the femoral regions, deformation of bones, etc. However, once the bone is decreased in bone quantity, it is difficult to restore the decreased bone quantity effectively. Therefore, it is most important to prevent the outbreak of osteoporosis and treat the osteoporosis at an early stage. Therefore, the development of a method for measuring bone mineral density capable of being widely used to treat osteoporosis at an early stage has become very important. Meanwhile, since the osteoporosis is generally systemic, the measurement of jawbone mineral density may be also the measure of the diagnosis of osteoporosis.

The methods for quantitatively measuring bone mineral density, which have been used in the art, include quantitative computed tomography (QCT), dual energy X-ray absorptiometry (DEXA), etc.

Since the quantitative computed tomography (QCT) is used to obtain a 3D image of bone, the QCT has advantages in that it is used to dividedly calculate the bone mineral density of cortical bone and trabecular bone, and also to predict the structural stability of the bones as well. However, since QCT equipment is very expensive and its radiation dose is high, the QCT equipment is not widely used in conventional methods for measuring bone mineral density.

The dual energy X-ray absorptiometry (DEXA) is widely used to measure 2-dimensional bone mineral density and determine the course of osteoporosis treatment since its equipment is cheaper than the QCT equipment, its radiation dose is low, and it shows high accuracy and excellent reproducibility in the measurement of the bone mineral density. However, it is impossible to use the conventional DEXA equipment to measure jawbone mineral density due to the structural characteristics of the DEXA equipment.

As described above, although the methods for measuring jawbone mineral density, such as QCT, have been used in the art, they have problems associated with the costs and the harmfulness of radiations. Therefore, it is necessary to develop a method for measuring jawbone mineral density using the jawbone X-ray image but not the QCT. On the other hand, the jawbone mineral density measurement method using a jawbone X-ray image is useful because most of dental clinics basically possess jawbone X-ray imaging equipment and the jawbone X-ray imaging is performed daily in dental procedures.

Also, the measurement of jawbone mineral density is required even in the prevailing artificial tooth transplantation procedures. Like common bones, the jawbone is composed of cortical bone and inner trabecular bone. In transplanting an artificial tooth, a teeth ridge is first cut, a hole is made in the jawbone, and the artificial tooth is inserted into the hole. In this case, when the jawbone has insufficient cortical bone quantity and trabecular bone quantity, the artificial tooth is not firmly fixed in the jawbone, which leads to a low success rate of the tooth transplantation. Therefore, it is possible to significantly reduce the failure rate of the transplantation of artificial teeth by measuring jawbone mineral density prior to the transplantation of the artificial teeth.

Nonetheless, there are no alternatives except for the dental CT equipment as means that can actually measure the jawbone mineral density. In the dental clinics that do not possess the dental CT equipment, doctors generally judge a dental panoramic image or a jawbone X-ray image from their experience to determine the reasonability of the transplantation of artificial teeth.

Several clinical methods for calculating bone mineral density from a dental panoramic image or a jawbone X-ray image have been proposed up to date. However, since most of the clinical methods are qualitative, they have the low accuracy in measuring the jawbone mineral density. In the case of the dental panoramic image, jawbone shown in the image shows the effect of X-ray absorption due to the presence of neck bones or overlapped soft tissues in the rear of the oral cavity. Therefore, it is not easy to measure jawbone mineral density using the dental panoramic image. On the contrary, since the jawbone X-ray image has somewhat overlapped tissues and easily uses a quantitative phantom, the jawbone X-ray image is more easily used to measure jawbone mineral density. However, jawbone mineral density measurement method using the jawbone X-ray image is still difficult to be commercialized.

SUMMARY OF THE INVENTION

An aspect of the present invention provides a method for measuring jawbone mineral density using a jawbone X-ray image.

Another aspect of the present invention provides a method for measuring accurate jawbone mineral density from a jawbone X-ray image by using a support device to enhance the accuracy in the measurement of jawbone mineral density, and undergoing a correction procedure, when necessary.

According to an aspect of the present invention, there is provided a method for measuring jawbone mineral density. Here, the method includes: obtaining a jawbone X-ray image using a support device for jawbone; defining a region of interest from the obtained jawbone X-ray image; and measuring jawbone mineral density from the defined region of interest. Also, the method may further include: correcting an image of the defined region of interest.

In this case, the step of correcting an image of the defined region of interest may be performed using the relation between an average grey level and thickness data according to each stage of a phantom of the jawbone X-ray image.

Also, the step of measuring jawbone mineral density may be performed by calculating a jawbone mineral density index, which is set to an average grey level, from the corrected region of interest, or by measuring the jawbone mineral density index using the linear relation between a predetermined jawbone mineral density index and the jawbone mineral density.

According to another aspect of the present invention, there is provided a support device for measuring jawbone mineral density including an exterior case having at least one open side surface and having an empty space formed therein; and a pouch attached to the inner empty space of the exterior case and filled with gel- or liquid-type substance to fix teeth.

In this case, the support device may further include an image acquisition unit formed in one outer side surface of the exterior case, and the image acquisition unit may be at least one selected from the group consisting of an X-ray film and a digital X-ray image sensor.

Also, the support device may further include a phantom formed in an inner side of the exterior case corresponding to the image acquisition unit, the phantom may be composed of a plurality of stages, and the phantom may have a horizontal groove and a vertical groove that are on the top and bottom of one stage out of the plurality of stages, respectively. In addition, a line between the midpoint of the horizontal groove formed in the phantom and the midpoint of the vertical groove may be vertical to upper and lower surfaces of the phantom.

Additionally, the exterior case may be formed in the shape of Korean letter 'ㄷ.'

According to still another aspect of the present invention, there is provided a computer-readable recording medium including a program that is used to execute the steps of obtaining a jawbone X-ray image using a support device for jawbone; defining a region of interest from the obtained jawbone X-ray image; and measuring jawbone mineral density from the defined region of interest.

According to yet another aspect of the present invention, there is provided a system for measuring jawbone mineral density. Here, the system includes a support device having a pouch formed in an inner part of an exterior case to fix teeth in the exterior case and including a phantom formed in one inner side surface of the exterior case to obtain a jawbone X-ray image (including an image of the phantom) through an image acquisition unit provided in the one inner side surface of the exterior case; an input/output unit inputting the obtained jawbone X-ray image and outputting the results of the processed jawbone X-ray image; a storage unit storing information that is required to measure jawbone mineral density from the obtained jawbone X-ray image; and a microprocessor controlling operations of the support device, the input/output unit and the storage unit, defining a region of interest from the obtained jawbone X-ray image, correcting an image of the defined region of interest and measuring jawbone mineral density.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will now be described in detail with reference to the accompanying drawings. For the exemplary embodiments of the present invention, detailed descriptions of known functions and constructions that are related to the present invention are omitted for clarity when they are proven to make the gist of the present invention unnecessarily confusing.

Figure 1:
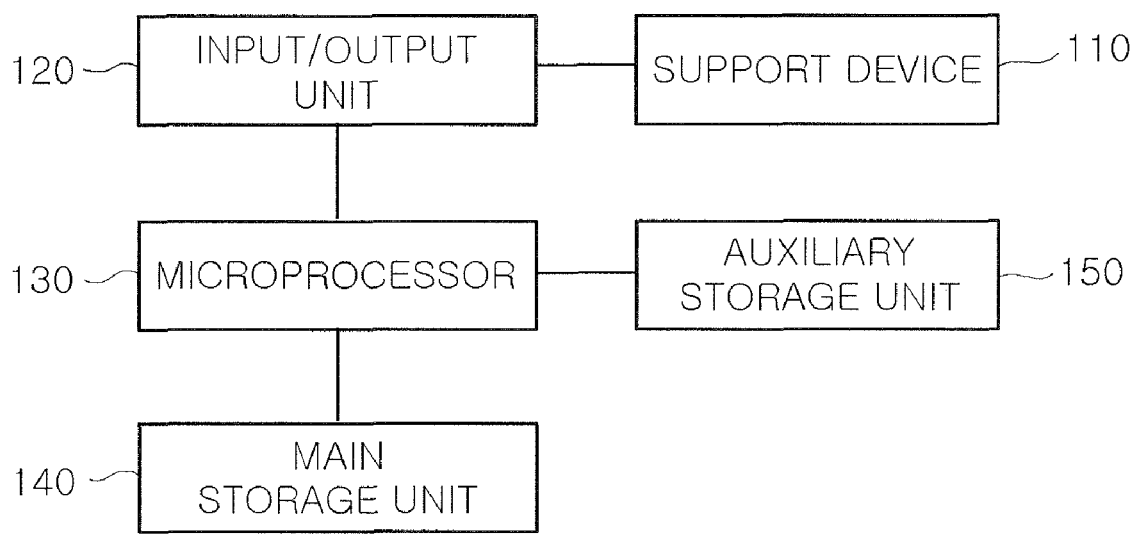
FIG. 1 is a diagram illustrating a configuration of a system for measuring jawbone mineral density according to one exemplary embodiment of the present invention.

FIG. 1 is a diagram illustrating a configuration of a system for measuring jawbone mineral density according to one exemplary embodiment of the present invention.

The system for measuring jawbone mineral density as shown in FIG. 1 includes a support device 110 for measuring jawbone mineral density, an input/output unit 120 for inputting/outputting data that are required to measure jawbone mineral density, a main storage unit 140 and an auxiliary storage unit 150 for storing information that is required to measure jawbone mineral density, and a microprocessor 130 controlling operations of the input/output unit 120 and the main/auxiliary storage units 140 and 150 and performing general arithmetic operations to measure jawbone mineral density using a jawbone X-ray image.

Figure 2:
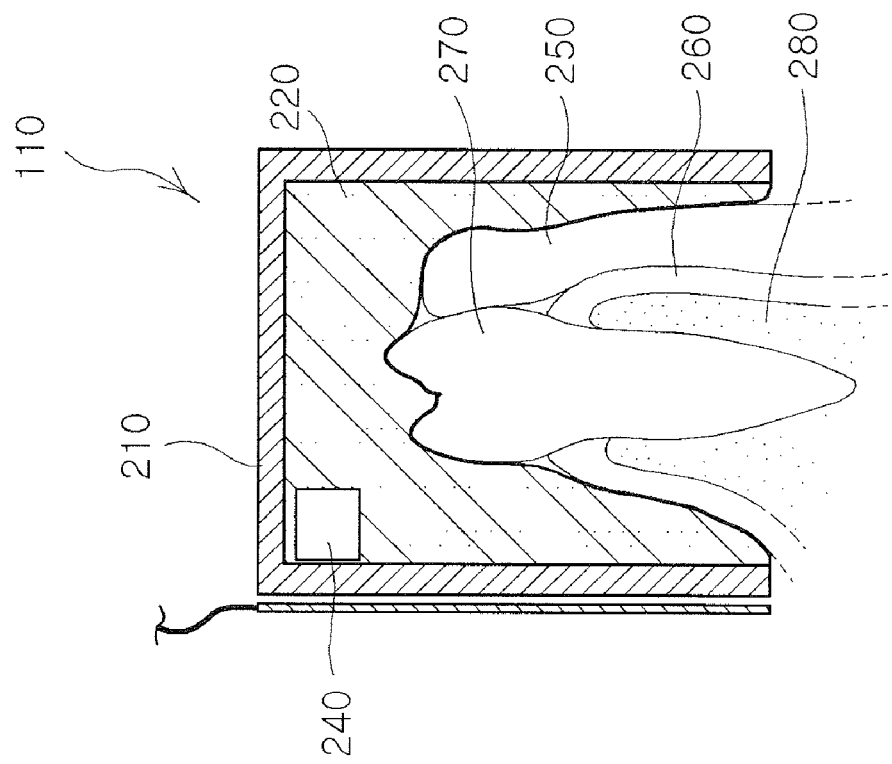
FIG. 2 is a diagram illustrating a configuration of a support device for measuring jawbone mineral density used in the present invention.
Figure 2:
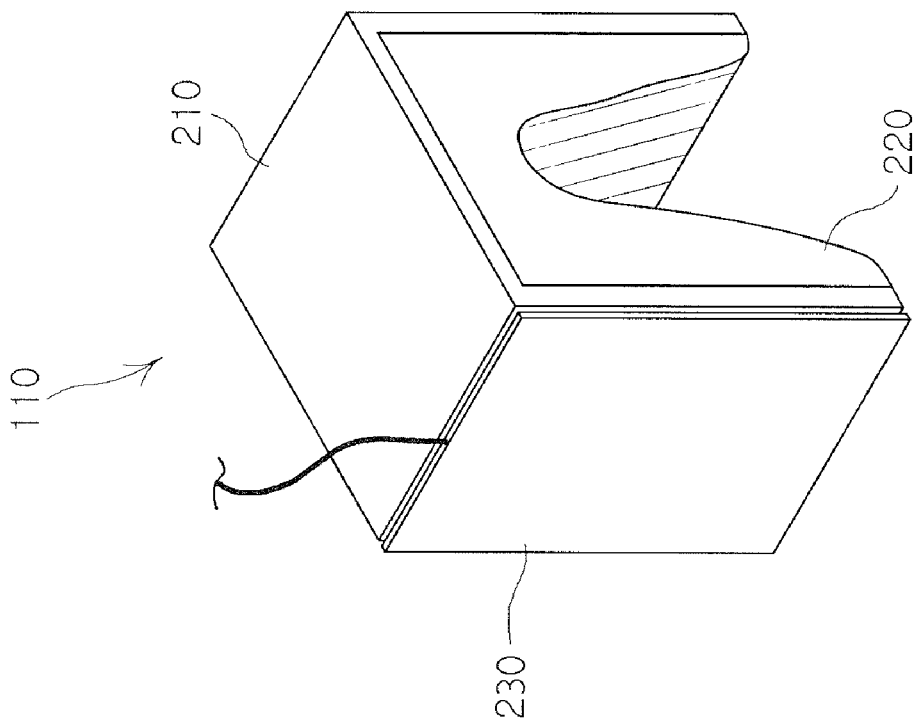

In order to measure jawbone mineral density from a jawbone X-ray image, the support device 110 includes components as shown in FIG. 2. Here, the components of the support device 110 are described in more detail with reference to FIGS. 2 and 3.

The input/output unit 120 functions to input information, which a user inputs in order to measure the jawbone mineral density, and a jawbone X-ray image obtained using a support device. The input unit may include a film and digital X-ray image sensor, each of which is provided in the support device 110, and the output unit may include a monitor, a printer, etc.

The main storage unit 140 and the auxiliary storage unit 150 store a variety of information required for the measurement of jawbone mineral density, for example, information set to define a region of interest from the jawbone X-ray image, information required for the correction of an image of the region of interest, and information required to calculate an actual jawbone mineral density from a jawbone mineral density index calculated from the region of interest.

The microprocessor 130 controls operations of the input/output unit 120 and the main/auxiliary storage units 140 and 150, and also has a program formed therein, the program executing the step of measuring jawbone mineral density from the obtained jawbone X-ray image. Here, the microprocessor 130 functions to measure the jawbone mineral density from the jawbone X-ray image by executing the built-in program. The measurement of jawbone mineral density from the jawbone X-ray image is described in detail with reference to FIG. 4.

FIG. 2 is a diagram illustrating a configuration of a support device for measuring jawbone mineral density used in the present invention.

In order to obtain a jawbone X-ray image, the support device 110 for measuring jawbone mineral density includes an exterior case 210, a pouch 220, an image acquisition unit 230 and a phantom 240.

The exterior case 210 has at least one open side surface to fix teeth, and has an empty space formed therein. For example, FIG. 2 shows an exterior case 210 in the shape of Korean letter 'ㄷ.' The exterior case 210 is formed of materials, such as plastic, which have similar X-ray absorption characteristics to human soft tissues. For example, the exterior case 210 may be made of acrylic materials.

An inner part of the exterior case 210 is provided with a pouch 220 filled with gel- or liquid-type X-ray soft-tissue equivalent substance. Water may be used as the X-ray soft-tissue equivalent substance, but the present invention is not particularly limited thereto. Therefore, a variety of materials may be used herein.

The image acquisition unit 230 may be provided in one outer side surface of the exterior case 210. The image acquisition unit 230 may include an X-ray film or a digital X-ray image sensor.

The support device 110 for measuring jawbone mineral density, as prepared thus, fixes teeth inside the support device 110 and performs X-ray photographing in order to obtain a jawbone X-ray image. An X-ray dose is decreased by the exterior case 210 of the support device, the soft equivalent substance in the pouch 220, lips 250, teethridge 260, teeth 270 and jawbone 280, and finally an X-ray image is formed on the X-ray film or digital X-ray image sensor of the image acquisition unit 230.

A constant tube voltage (kVp) of an X-ray generator should be maintained in order to obtain a jawbone X-ray image. For example, a tube voltage of the X-ray generator may be maintained to a level of 60 kVp. The jawbone X-ray image may be merely obtained by using an X-ray film or a digital X-ray image sensor. Here, an X-ray film may be digitalized with a film to obtain a jawbone X-ray image, and the digital X-ray image sensor may be directly used to obtain a jawbone X-ray image without the use of the film. Also, the spatial resolution of the image may be set to a level of 200PPI (pixels per inch), and each pixel value may be set to 256 grey levels.

Image characteristics of the jawbone X-ray image such as brightness and contrast ratio is sensitive to the changes in X-ray image acquisition conditions (milliamperes (mAs) of an X-ray generator, a distance to an X-ray source, and the like). That is, the brightness (grey levels) of each pixel in the X-ray image may not be an absolute standard of the absorbed X-ray dose in corresponding pixels. Therefore, when the X-ray image is used to measure bone mineral density, it is, first of all, desirable to correct the changes in the image characteristics of the jawbone X-ray image according to the X-ray image acquisition conditions. Accordingly, the phantom 240 is attached to the support device 110 for measuring jawbone mineral density in order to quantitatively correct the obtained jawbone X-ray image, as shown in FIG. 2.

Figure 3:
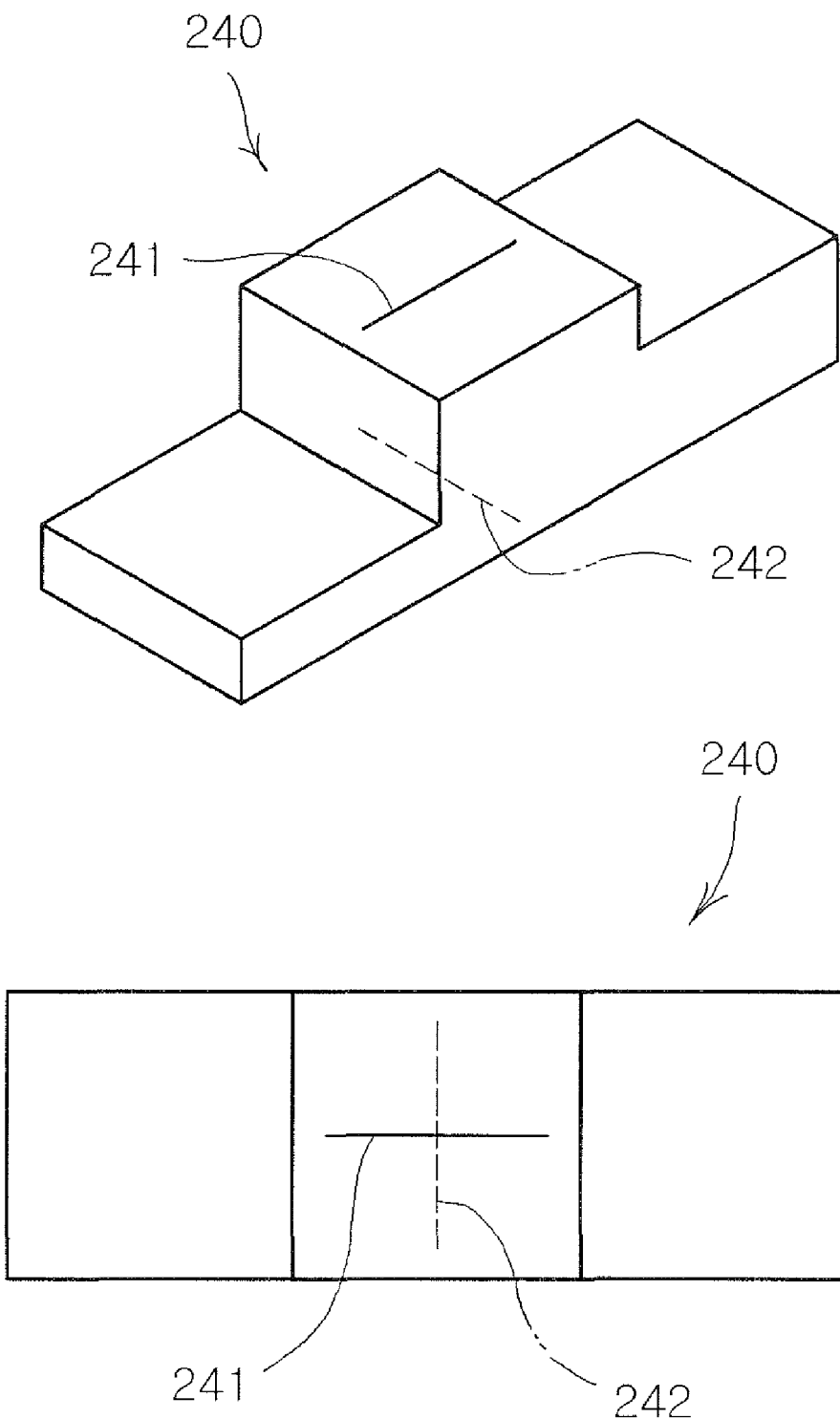
FIG. 3 is a diagram illustrating a configuration of a phantom attached to the support device.

FIG. 3 is a diagram illustrating a configuration of a phantom attached to the support device.

The phantom 240 used to correct the jawbone X-ray image is fixedly installed in an inner part of the exterior case 210. Aluminum is generally used as the materials of the X-ray phantom, but the present invention is not particularly limited thereto. A thickness of the aluminum phantom may be suitably selected according to a region for measuring the bone mineral density. When a region used to measure the bone mineral density is jawbone, it is preferred to set a maximum thickness of the aluminum phantom to 6 mm. The X-ray phantom 240 as shown in FIG. 3 has the base side of 7 mm×21 mm, and three stages having heights of 2, 6 and 4 mm, respectively.

Meanwhile, when the X-ray phantom is used to correct the image, information on the thickness of each stage of the X-ray phantom is required. In case X-rays are not irradiated vertically to the phantom 240, the thickness of the phantom may be varied, which leads to inaccurate correction of the image. Also, when the X-ray film or the digital X-ray sensor attached to the phantom 240 is disposed aslant to the irradiation axis of X-ray beam, the brightness of the X-ray image may be severely distorted due to the uneven intensity of the X-ray beam. In order to solve the above-mentioned problems, a horizontal groove 241 and a vertical groove 242 are formed on the top and bottom of one stage (hereinafter, a 6 mm stage) of the phantom so that they can be met at a right angle, as shown in FIG. 3, thereby forming a cross-type pattern on the jawbone X-ray image. Here, the horizontal and vertical grooves formed on the top and bottom of the phantom 240 preferably have the same length as each other. Therefore, when seen from right above with respect to the phantom 240, the horizontal and vertical grooves are preferably divided into two equal parts. This type of the phantom is attached to the support device 110 to photograph a jawbone X-ray image, an image of the phantom 240 appears on the jawbone X-ray image, and a cross-type pattern is formed on the 6 mm stage of the phantom 240. As seen from the jawbone X-ray image, an angle $\theta=\tan^{-1}(D/T)$ between a distance (D, between the centers of a horizontal pattern and a vertical pattern) and a thickness (T) of the patterned stage of the phantom 240 should be within several degrees (for example, $\theta=10$). This is because when the X-ray source is irradiated highly aslant to the phantom 240 and the image acquisition unit 230 such as a X-ray film or a digital X-ray sensor, the X-ray image may be severely distorted, which leads to the low accuracy in the measurement of the bone mineral density. In this case, a jawbone X-ray image should be re-photographed after arrangement of the irradiation axis of the X-ray source.

Figure 4:
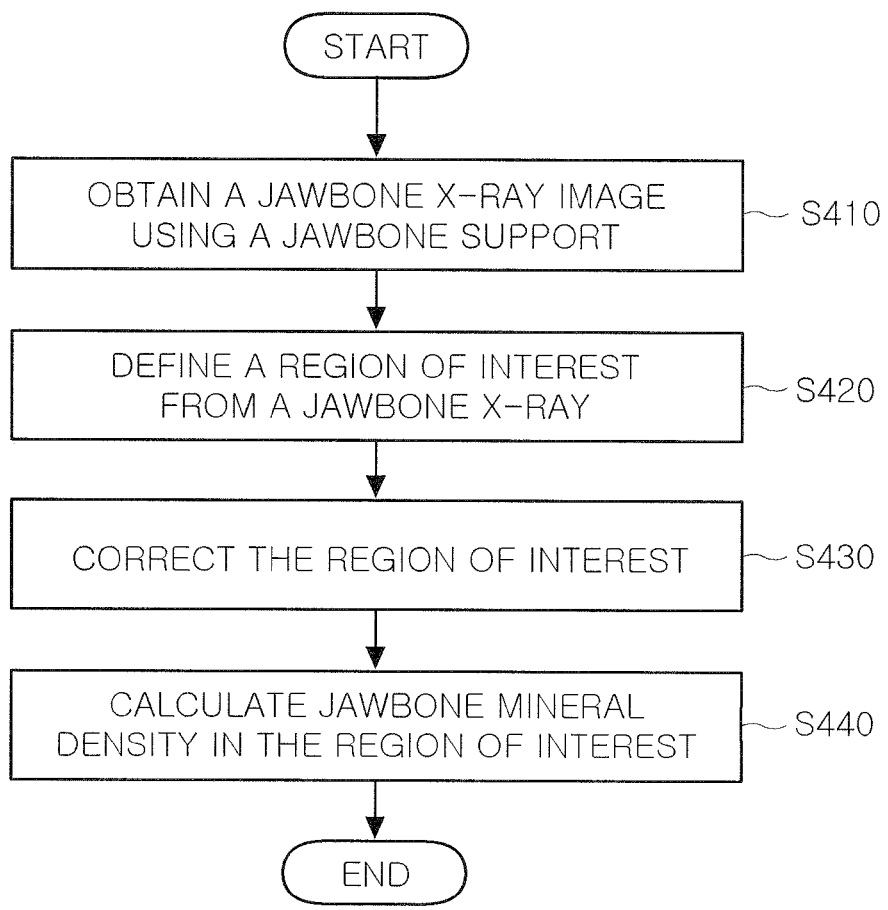
FIG. 4 is a flowchart illustrating a method for measuring jawbone mineral density according to one exemplary embodiment of the present invention.

FIG. 4 is a flowchart illustrating a method for measuring jawbone mineral density according to one exemplary embodiment of the present invention.

According to the method for measuring jawbone mineral density using a support device, first, the support device is used to obtain a jawbone X-ray image (S410). The jawbone X-ray image is obtained in the image acquisition unit 230 provided in one side of the exterior case 210 of the support device 110. The X-ray image taken in the image acquisition unit 230 may be used to analyze an image of the phantom 240. If necessary, the photographing conditions may be changed to obtain an optimal jawbone X-ray image.

Figure 5:
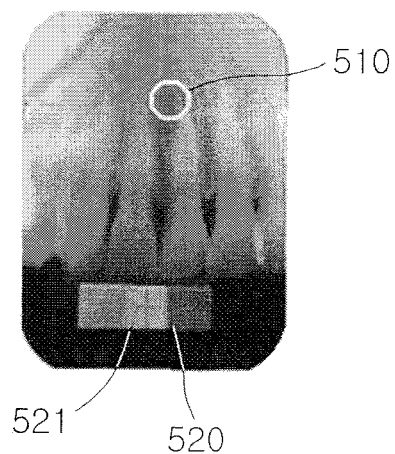
FIG. 5 is a diagram illustrating one example of a jawbone X-ray image according to one exemplary embodiment of the present invention.

When the jawbone X-ray image is obtained at the image acquisition unit 230, a region that is used to measure bone mineral density is set as a region of interest in the obtained jawbone X-ray image (S420). The region of interest may be defined in the form of a rectangle, a square and a circle. Here, the region of interest may be defined in the form of a circle, as shown in FIG. 5. For example, the region of interest is defined in the form of a circle with a radius of 25 pixels. In order to define the region of interest, specific data on a position, a shape and a size of the region of interest may be determined and stored in the main/auxiliary storage unit in advance.

When a region of interest used to measure the bone mineral density is set from the jawbone X-ray image, the X-ray phantom image may be used to correct an image of the region of interest, thus to enhance the accuracy in the measurement of the jawbone mineral density (S430). Then, an average grey level of each stage of the X-ray phantom image 520 is measured to correct the region of interest.

Meanwhile, in measuring an average grey level of the cross-type patterned region 521, an effect of the cross-type pattern should be removed. As a result, an additional procedure is performed, as follows. First, a measuring region for measuring an average grey level is set from the cross-type patterned region 521, and a histogram is analyzed. The histogram has two peaks formed therein. Here, the cross-type patterned region corresponds to the darker peak. A suitable value (for example, an intermediate value) between the two peaks is set to a threshold value, and an average grey level of pixels having a brighter grey level than the threshold value is set to an average grey level of the stage. Then, the average grey level and thickness data of each stage of the X-ray phantom image are used to correct an image of the region of interest. In order to correct the image of the region of interest, an equation $[g=f(t)]$ between a thickness (t) and an average grey level (g) of the phantom should be obtained. The equation is obtained using polynomial fitting of the data, using function fitting such as tanh, or using a piecewise linear relation. In order to correct pixels in the region of interest, a converted thickness $[f^{-1}(g)]$ of the phantom corresponding to the brightness of the pixels is calculated. When the converted thickness of the phantom is less than 0 mm, a grey level is corrected to a level of 0, whereas when the converted thickness of the phantom exceeds the maximum thickness of 6 mm, the grey level is corrected to a level of 255, and in other cases, the grey level is corrected to an integer of $255*f^{-1}(g)/6.0$.

After the correction of the region of interest 510, the jawbone mineral density of the region of interest 510 is measured (S440). In order to measure the jawbone mineral density from the region of interest, first, a jawbone mineral density index is calculated. The jawbone mineral density index is set to an average of grey levels of the corrected region of interest. Meanwhile, the jawbone mineral density index may be directly used as the jawbone mineral density, and actually be converted into the actual jawbone mineral density. For a plurality of subjects, the jawbone mineral density and the jawbone mineral density index of the region of interest are measured using QCT equipment and the method according to the present invention, respectively, in order to actually convert the jawbone mineral density index into the actual jawbone mineral density. Then, a linear relation between the QCT jawbone mineral density and the jawbone mineral density index, as measured from the plurality of subjects, is deduced to actually convert the jawbone mineral density from the jawbone mineral density index. Therefore, information on the linear relation between jawbone mineral density index and jawbone mineral density as calculated in advance by a plurality of subjects should be stored in the main/auxiliary storage units in order to convert the jawbone mineral density index to the actual jawbone mineral density.

The present invention may also be realized with computer-readable codes in computer-readable recording media. The computer-readable recording media include all kinds of recording devices in which data that are readable by computer systems are stored. Examples of the computer-readable recording media include ROMs, RAMs, CD_ROMs, magnetic tapes, floppy disks and optical data storage devices. Also, the computer-readable recording media include devices that are realized in the form of a carrier wave (i.e., transmissions through internet). Also, the computer-readable recording media are shared with the computer systems connected via internet. Therefore they may be stored in the form of computer-readable codes and executed in a sharing manner.

As described above, the method for measuring jawbone mineral density according to one exemplary embodiment of the present invention may be useful to enhance the accuracy in the measurement of the jawbone mineral density measure by employing the support device for jawbone to maintain a constant effect on soft tissues and using a built-in X-ray phantom to quantify the X-ray absorbance and remove carelessly photographed jawbone X-ray images.

Also, the method for measuring jawbone mineral density according to one exemplary embodiment of the present invention may be useful to check up the outbreak of osteoporosis cheaply and easily since the jawbone mineral density may be measured with jawbone X-ray imaging devices that have been widely used in dental clinics While the method and support device for measuring jawbone mineral density have been shown and described in connection with the exemplary embodiments of the present invention, it will be apparent to those skilled in the art that modifications and variations can be made without departing from the scope of the invention as defined by the appended claims. Accordingly, it should be understood that the present invention is not limited to the exemplary embodiments and the accompanying drawings since various changes and modifications within the scope of the invention will become apparent to those skilled in the art from this detailed description.

What is claimed is:

1. A method for measuring jawbone mineral density, the method comprising:
   positioning a support device for jawbone covering portions of teeth, lip, teethridge, and jawbone;
   obtaining a jawbone X-ray image using the support device for jawbone;
   defining a region of interest from the obtained jawbone X-ray image; and
   measuring jawbone mineral density from the defined region of interest.

2. The method of claim 1, further comprising: correcting an image of the defined region of interest.

3. The method of claim 2, wherein the step of correcting an image of the defined region of interest is performed using the relation between an average grey level and thickness data according to each stage of a phantom image of the jawbone X-ray image.

4. The method of claim 3, wherein the step of measuring jawbone mineral density is performed by calculating a jawbone mineral density index, which is set to an average grey level, from the corrected region of interest.

5. The method of claim 4, wherein the step of measuring jawbone mineral density is performed by measuring a jawbone mineral density from the calculated jawbone mineral density index by using a predetermined linear relation between a jawbone mineral density index and an actual jawbone mineral density.

6. A support device for measuring jawbone mineral density, comprising:
   an exterior case having at least one open side surface and having an empty space formed therein wherein the exterior case covers portions of each of teeth, lip, teethridge, and jawbone; and
   a pouch attached to the inner empty space of the exterior case and filled with gel or liquid substance to fix the support device with respect to teeth inside the exterior case.

7. The support device of claim 6, further comprising an image acquisition unit formed in one outer side surface of the exterior case.

8. The support device of claim 7, wherein the image acquisition unit is at least one selected from the group consisting of an X-ray film and a digital X-ray image sensor.

9. The support device of claim 7, further comprising a phantom formed in an inner side of the exterior case corresponding to the image acquisition unit.

10. The support device of claim 9, wherein the phantom is composed of a plurality of stages.

11. The support device of claim 10, wherein the phantom has a horizontal groove placed in one of the top and bottom surfaces of any one of the plurality of stages, and a vertical groove placed in the remaining one of the top and bottom surfaces, the horizontal and vertical grooves crossing each other at a right angle when viewed from the top.

12. The support device of claim 11, wherein a line between the midpoint of the horizontal groove and the midpoint of the vertical groove is perpendicular to top and bottom surfaces of the phantom.

13. The support device of claim 6, wherein the exterior case is formed in the shape of Korean letter 'ㄷ.'

14. The support device of claim 6, wherein the pouch attached to the inner empty space of the exterior case covers portions of each of teeth, lip, teethridge, and jawbone.

15. A system for measuring jawbone mineral density, the system comprising:

a support device having a pouch formed in an inner part of an exterior case to fix the support device with respect to teeth inside the exterior case and including a phantom formed in one inner side surface of the exterior case wherein the exterior case covers portions of each of teeth, lip, teethridge, and jawbone;

an image acquisition unit provided in an outer side surface of the exterior case to obtain a jawbone X-ray image including an image of the phantom;

an input/output unit inputting the obtained jawbone X-ray image and outputting the results of the processed jawbone X-ray image;

a storage unit storing information that is required to measure jawbone mineral density from the obtained jawbone X-ray image; and a microprocessor controlling operations of the support device, the input/output unit and the storage unit, defining a region of interest from the obtained jawbone X-ray image, correcting an image of the defined region of interest and measuring jawbone mineral density.

16. The system of claim 15, wherein the phantom is composed of a plurality of stages, wherein one stage of the plurality of stages has a horizontal groove on a top side and a vertical groove on a bottom side.

* * * * *